United States Patent [19]
Watson et al.

[11] Patent Number: 6,158,436
[45] Date of Patent: Dec. 12, 2000

[54] PATIENT CONSTRAINT

[76] Inventors: Wesley S. Watson; Mary S. Watson, both of P.O. Box 877, Oatman, Ariz. 86433

[21] Appl. No.: 09/574,247

[22] Filed: May 19, 2000

Related U.S. Application Data

[60] Provisional application No. 60/136,216, May 26, 1999.
[51] Int. Cl.[7] .................................................. A61B 19/00
[52] U.S. Cl. .......................... 128/869; 128/872; 128/874; 602/19
[58] Field of Search ...................... 128/846, 869, 128/870, 872, 873, 874, 876, 875; 602/5, 19

[56] References Cited

U.S. PATENT DOCUMENTS

| | | |
|---|---|---|
| 4,877,038 | 10/1989 | Fricke et al. . |
| 5,072,725 | 12/1991 | Miller ........................................ 602/19 |
| 5,158,531 | 10/1992 | Zamosky ...................................... 602/5 |
| 5,259,831 | 11/1993 | LuBron ...................................... 602/19 |
| 5,451,200 | 9/1995 | LaBella ......................................... 2/45 |
| 5,533,163 | 7/1996 | Hall ........................................ 602/19 |
| 5,549,121 | 8/1996 | Vinci . |
| 5,558,102 | 9/1996 | McCarthy . |
| 5,664,581 | 9/1997 | Ashley . |
| 5,832,928 | 11/1998 | Padilla, Jr. . |

*Primary Examiner*—Michael A. Brown

[57] ABSTRACT

A patient restraint for gathering and retaining the limbs of a patient, and for retaining tubes of medical equipment on the body of the patient. The restraint includes a rectangular flexible base panel lined with hook and loop fastener, and three straps lined with complementing hook and loop fastener. The base panel is sufficiently long as to be able to wrap almost entirely around an adult human torso. The width is half the magnitude of the length. The straps are limited in length to half the length of the base panel and in width to one tenth that of the base panel. One of the straps is shorter and narrower than are the other two straps.

5 Claims, 2 Drawing Sheets

PATIENT CONSTRAINT

REFERENCE TO RELATED APPLICATION

This application is a continuation of Provisional Patent Application Serial No. 60/136,216, filed May 26, 1999.

BACKGROUND OF THE INVENTION

1. Field of the Invention

The present invention relates to a medical support or constraint for gathering and retaining the limbs of a patient receiving emergency medical assistance, and for retaining tubes of medical equipment to the patient. The support comprises a flexible fabric and a plurality of straps which detachably engage the fabric by hook and loop fastener.

2. Description of the Prior Art

In medical emergencies such as accidents and sudden debilitating events such as heart attacks, emergency medical personnel may be required to attach tubes to conduct blood components and other therapeutic fluids to the patient. In an emergency situation, emergency personnel may not have facilities available at a hospital, and thus may lack even elementary equipment for securing tubes to the patient, for keeping the patient's limbs secured to the body, and for similar purposes. The patient is susceptible to having his or her limbs and medical equipment snag on environmental objects or otherwise be lost, disconnected, and entangled. It may then be difficult or impossible to place the patient on a gurney for transport to a hospital. Even if emergency personnel are able to properly restrain and contain medical equipment and the patient's limbs, without appropriate equipment, this process may consume valuable time. Spending time for auxiliary functions may in extreme instances be the difference between life and death.

The prior art has recognized the necessity of securing auxiliary equipment to a patient. Various devices employing straps have been proposed for addressing certain specific situations in the medical field. U.S. Pat. No. 4,877,038, issued to Eberhard Fricke et al. on Oct. 31, 1989, describes a hand and arm restraint for patients. The restraint comprises a rectangular fabric panel having straps projecting from two corners and another, separate strap which can be passed through eyes located at the other two corners. By contrast, the present invention has a base panel and separate, attachable straps.

U.S. Pat. No. 5,549,121, issued to Vincent A. Vinci on Aug. 27, 1996, describes an arm support comprising a flexible fabric intended to support a patient's arms during a medical diagnostic or remedial procedure. The fabric is formed as an elongate strip bearing hook and loop fasteners at certain points, to enable the strip to be folded over and adhered to itself. There are no separate straps associated with the device of Vinci, as provided in the present invention.

U.S. Pat. No. 5,558,102, issued to Andrew D. McCarthy on Sep. 24, 1996, describes a restraint harness comprised entirely of straps. The straps attach to one another at removable attachment points by buckles or loops. There is no base panel having attachment structure for the straps, as seen in the present invention.

U.S. Pat. No. 5,664,581, issued to John P. Ashley on Sep. 9, 1997, describes a securing strap intended to control intravenous tubing connected to an injection port. The securing strap comprises a relatively large base panel and two smaller straps. The smaller straps attach to the base panel by hook and loop fastener. Configuration and proportions of the components of the device of Ashley differ from those of the present invention.

U.S. Pat. No. 5,832,928, issued to James D. Padilla, Jr. on Nov. 10, 1998, describes a securement device for securing intravenous tubing on a patient. Upper and lower sections of the device are secured in place by straps bearing hook and loop fastener. Configuration and proportions of the components of the device of Padilla, Jr. differ from those of the present invention.

None of the above inventions and patents, taken either singly or in combination, is seen to describe the instant invention as claimed.

SUMMARY OF THE INVENTION

The present invention sets forth apparatus which can quickly and easily be deployed to restrain and gather a patient's limbs in an emergency situation wherein the patient is to be transported to a medical facility. The invention addresses the problem of keeping body limbs and medical equipment such as tubes close to the body to avoid snagging on environmental objects as the patient is carried about, and of possibly losing and disconnecting tubes and other medical equipment especially when medical personnel are moving hastily to rush the patient to the medical facility. The invention enables this practical aspect of medical care to be performed expeditiously.

The apparatus includes a base panel formed from strong, flexible fabric which encircles the body and a plurality of flexible straps which readily fasten to and remove from the panel. The base panel and straps have complementing patches of hook and loop fastener material to enable ready installation and removal of the straps. The patient or a major limb of the patient is placed on the base panel and is secured in place by the straps. A similar procedure is employed to entrap and retain tubes and other medical equipment attached to the body.

Accordingly, it is one object of the invention to provide apparatus for keeping a patient's limbs and auxiliary medical equipment close to the body.

It is another object of the invention to enable expeditious securement of the patient's limbs and auxiliary medical equipment.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

The present invention sets forth apparatus for restraining and containing a patient's limbs as well as tubes and other ancillary devices employed in emergency medical procedures. The apparatus is intended to be placed over, under, or around the body, and held there by straps. Tubes and the like are retained by some straps, and other straps secure the apparatus.

Figure 1:
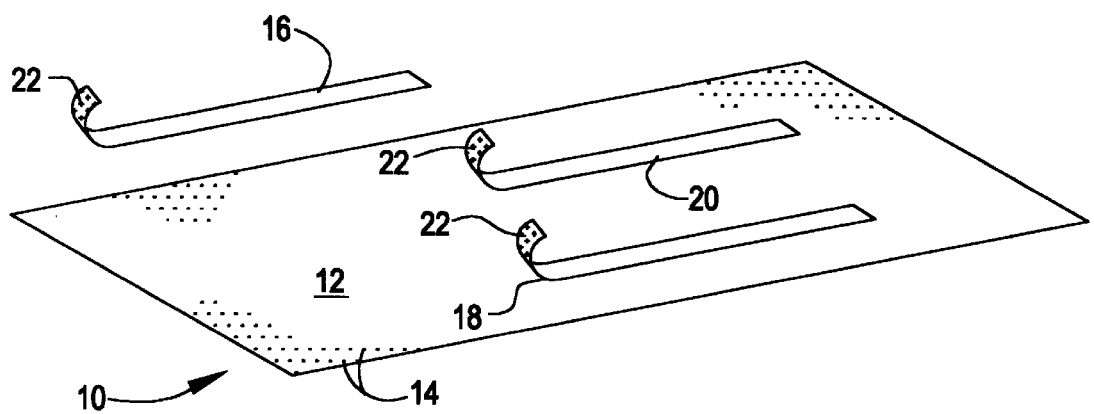
FIG. 1 is an exploded, top perspective view of the invention.

Turning now to FIG. 1, the novel apparatus comprises a generally rectangular panel 10 of flexible material bearing on its upper side 12 hooks 14 of hook and loop fastener material. Upper side 12 is entirely covered with hooks 14. Three straps 16, 18, 20 are provided. Straps 16, 18 are longer and wider than strap 20. Each strap 16, 18, or 20 bears on one side loops 22 of hook and loop fastener. Each strap 16, 18, or 20 can therefore be removably adhered to panel 10.

Figure 2:
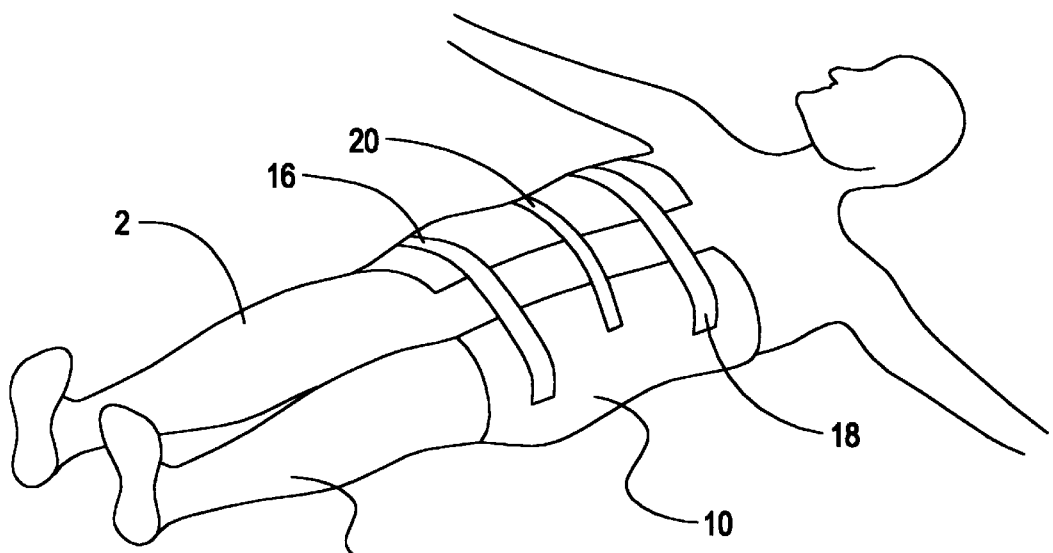
FIG. 2 is an environmental, perspective view showing a first representative application of the invention.

Configuration and proportions of straps 16, 18, 20 are selected to enable many different body and equipment positions to be accommodated. As shown in FIG. 2, panel 10 is placed under a patient with straps 16, 18, 20 disposed to close a partial loop formed by panel 10. In this application, the invention keeps the legs 2 of the patient from separating. This is highly useful in maintaining equilibrium and control when transporting a supine patient on a gurney.

Figure 3:
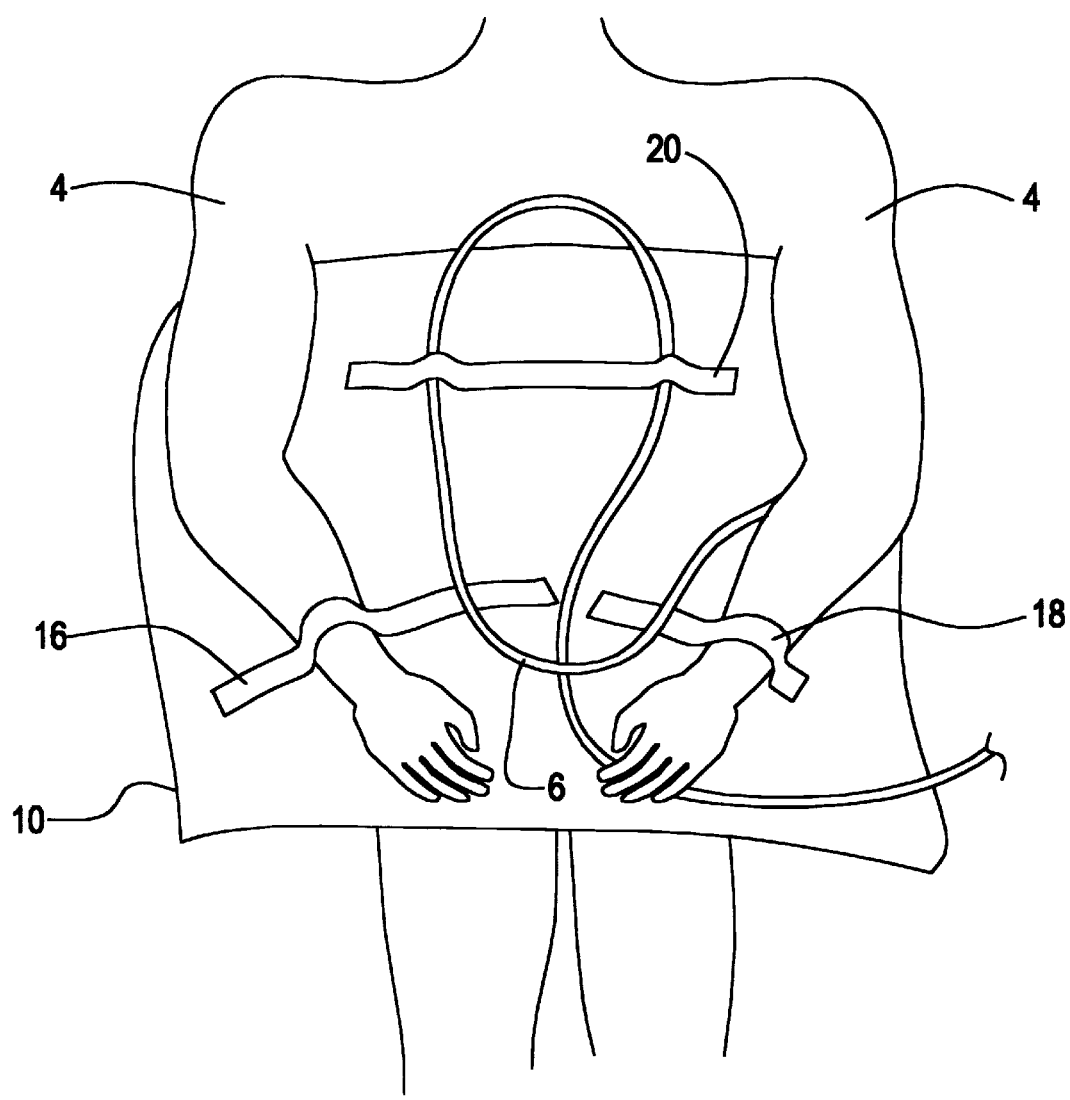
FIG. 3 is an environmental, perspective view showing a second representative application of the invention.

FIG. 3 illustrates a different situation wherein a patient's arms 4 must be held to the torso. A breathing tube 6 or the like is secured to panel 10 with slack taken up by arranging tube 6 so that strap 20 crosses it at two points, thereby immobilizing tube 6. Straps 16, 18 are passed over the arms 4 and are pressed into engagement with panel 10 so that the arms 4 are secured in a natural, comfortable position.

To accomplish the usages shown in FIGS. 2 and 3, the following dimensions and relationships are necessary. Panel 10 is sufficiently long as to wrap almost entirely around an adult torso 8, as shown in FIG. 2. Width of panel 10 is preferably about forty percent of the length of panel 10. Straps 16, 18 are preferably half of the length of panel 10, and the width of straps 16, 18 is roughly ten percent of the width of panel 10. Strap 20 is equal in length or slightly shorter than straps 16, 18, and preferably narrower.

In the preferred embodiment, width of strap 20 is roughly half that of straps 16, 18. These relationships assure that panel 10 be large enough to be useful in partially enveloping a human torso, but sufficiently small to be maneuverable and easy to stow in an ambulance or with other emergency equipment. Straps 16, 18 are sufficiently wide to be able to control the arm or leg of an adult human, and short enough to be positioned in various ways on panel 10 without having cumbersome excess length after being placed over limbs being contained or restrained. Strap 20 is smaller than straps 16, 18, so that it will be more suitable than straps 16, 18 for entrapping much smaller objects than human limbs, and being susceptible to fitting between and cooperating with straps 16, 18.

Any flexible, durable material will be suitable for forming panel 10 and straps 16, 18, 20. A preferred material is that known in the automotive trades as "trunk liner", which material is employed to form automobile dashboard covers. Hook and loop fastener is preferred since fastening positions of straps 16, 18, 20 relative to panel 10 are almost universal, and are readily manually removed and installed. It is not critical whether hooks or loops are fixed to panel 10, with the other or complementing member being provided on straps 16, 18, 20.

It is to be understood that the present invention is not limited to the embodiments described above, but encompasses any and all embodiments within the scope of the following claims.

I claim:

1. Apparatus for restraining and containing the limbs of a medical patient and ancillary devices employed in emergency medical procedures, comprising:

a flexible base panel having an upper side entirely covered with one member of hook and loop fastener, and a lower side; and a plurality of flexible straps each having one side covered with the complementing member of hook and loop material, wherein each one of said straps is limited in length to one half of the length of said base panel and is limited in width to one fifth of the width of said base panel.

2. The apparatus according to claim 1, wherein said base panel is sufficiently long as to wrap almost entirely around an adult torso, and the width of said base panel is limited to half the length of said base panel.

3. The apparatus according to claim 1, wherein said straps each have width limited to one tenth of the length of said base panel.

4. The apparatus according to claim 1, wherein at least two of said straps are of one length and at least one said strap is shorter and narrower than said two straps.

5. Apparatus for restraining and containing the limbs of a medical patient and ancillary devices employed in emergency medical procedures, comprising:

a flexible base panel sufficiently long as to wrap almost entirely around an adult torso, wherein the width of said base panel is limited to half the length of said base panel, and wherein said base panel has an upper side entirely covered with one member of hook and loop fastener, and a lower side; and at least three flexible straps each having one side covered with the complementing member of hook and loop material, wherein each one of said straps is limited in length to one half of the length of said base panel and is limited in width to one fifth of the width of said base panel, wherein at least two of said straps have length about half of that of said base panel and width of about one tenth that of said base panel, and at least one of said straps is shorter and narrower than are said two straps.

\* \* \* \* \*